United States Patent
Maksene

[11] Patent Number: 5,728,163
[45] Date of Patent: Mar. 17, 1998

[54] PHALANGEAL JOINT PROSTHESIS

[76] Inventor: Philippe Maksene, Clinique du Coudon, Chemin de la Coupiane, 83160 La Valette, France

[21] Appl. No.: 607,309

[22] Filed: Feb. 26, 1996

[30] Foreign Application Priority Data

Jan. 23, 1996 [FR] France .................. 96 01016

[51] Int. Cl.$^6$ .................................................. A61F 2/42
[52] U.S. Cl. .................................................. 623/21
[58] Field of Search .................. 623/21, 18, 22, 623/23, 16

[56] References Cited

U.S. PATENT DOCUMENTS

| | | | |
|---|---|---|---|
| 4,231,121 | 11/1980 | Lewis | 3/1.91 |
| 4,242,759 | 1/1981 | White | 3/1.91 |
| 4,366,183 | 12/1982 | Ghommidh et al. | 623/16 |
| 4,642,122 | 2/1987 | Steffee | 623/21 |
| 4,725,280 | 2/1988 | Laure | 623/21 |
| 4,731,087 | 3/1988 | Sculco et al. | 623/21 |
| 5,037,440 | 8/1991 | Koenig | 623/21 |
| 5,405,399 | 4/1995 | Tornier | 623/21 |
| 5,405,400 | 4/1995 | Linscheid et al. | 623/21 |
| 5,405,401 | 4/1995 | Lippincott, III et al. | 623/21 |
| 5,413,609 | 5/1995 | Nicol et al. | 623/21 |

FOREIGN PATENT DOCUMENTS

| | | |
|---|---|---|
| 0455929 | 11/1991 | European Pat. Off. . |
| 2701388 | 8/1994 | France . |
| 2705559 | 12/1994 | France . |
| 4330248 | 3/1995 | Germany . |
| 4337922 | 5/1995 | Germany . |
| 8906946 | 8/1989 | WIPO . |

*Primary Examiner*—David Isabella
*Attorney, Agent, or Firm*—Ladas & Parry

[57] ABSTRACT

This invention concerns phalangeal joint prosthesis; more specifically metacarpo-phalangeal or inter-phalangeal prostheses. A phalangeal joint prosthesis is made up of a head of a proximal element which comprises a first articular sliding surface and a base belonging to a distal element which includes a second articular sliding surface. This head and base are devoid of stops.

4 Claims, 2 Drawing Sheets

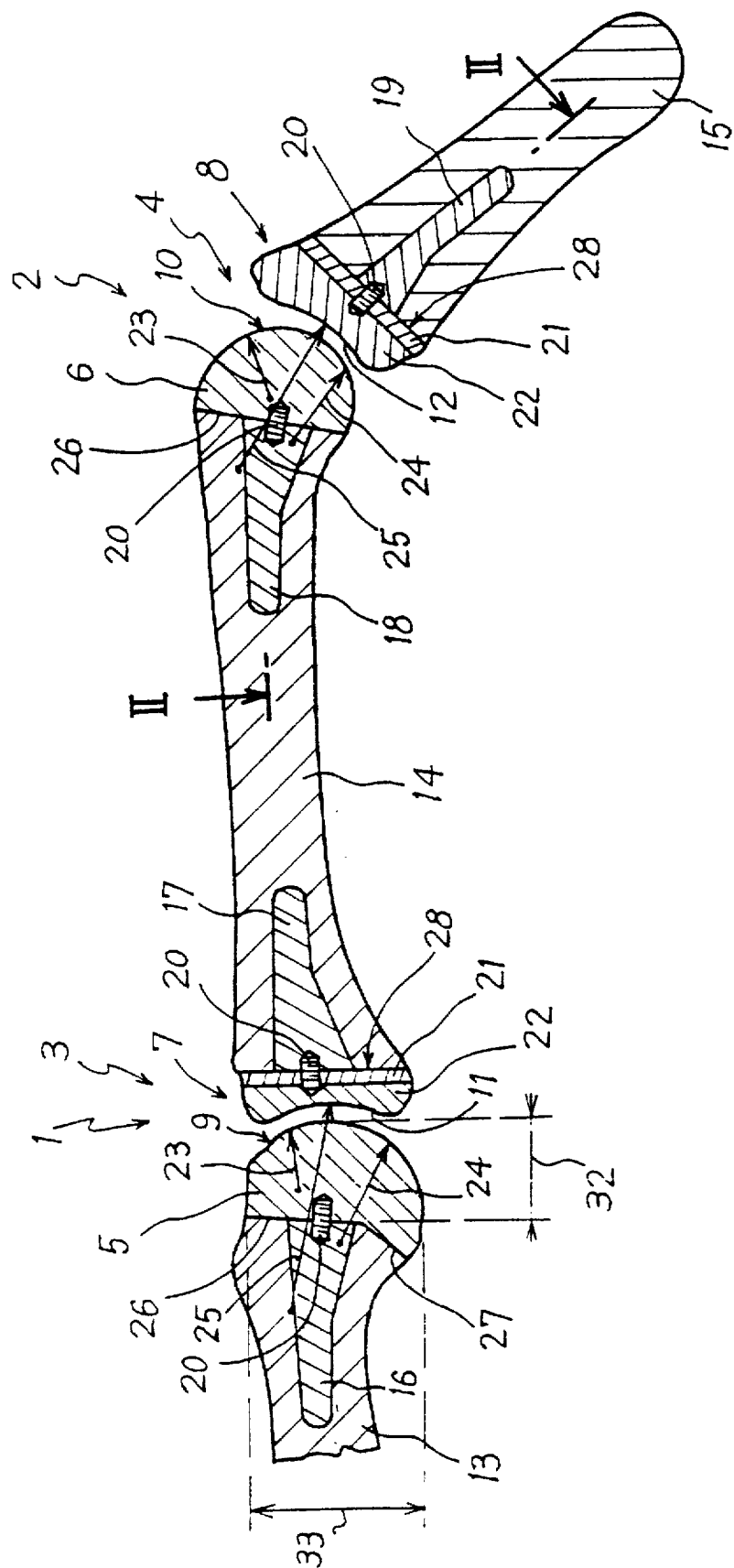
FIG_1

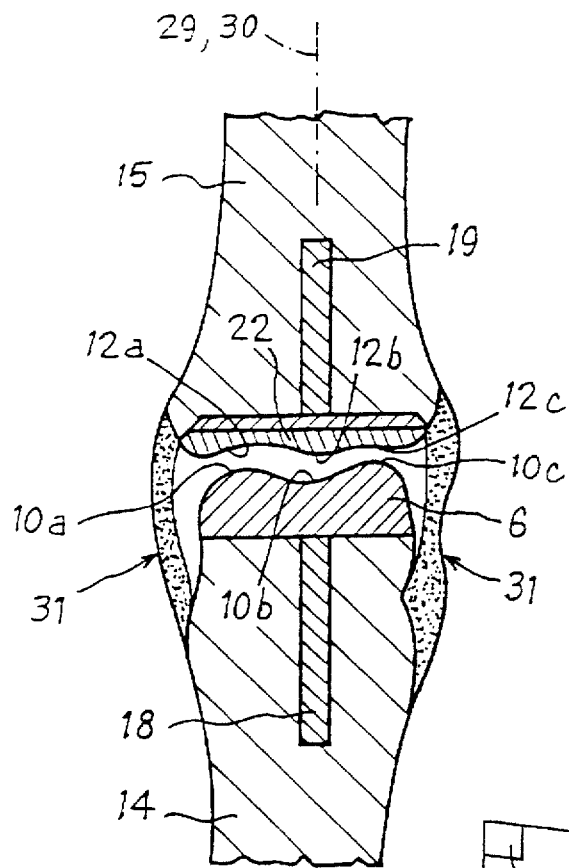
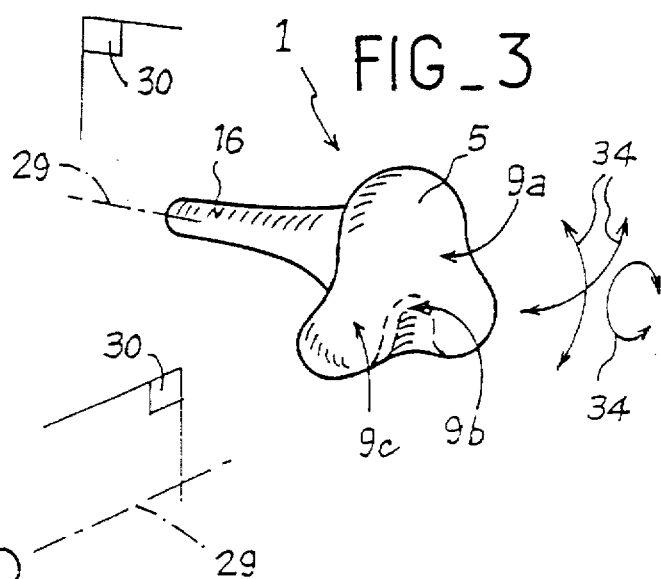
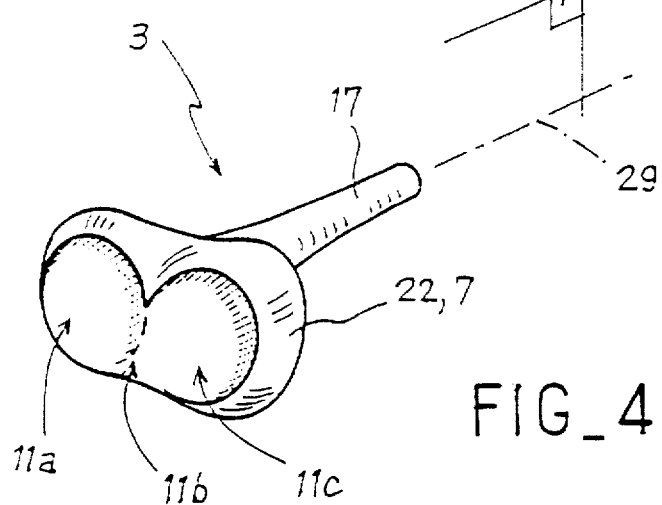

PHALANGEAL JOINT PROSTHESIS

BACKGROUND OF THE INVENTION

1. Field of the Invention

This invention concerns phalangeal joint prostheses, more specifically metacarpo-phalangeal joint prostheses, inter-phalangeal joint prostheses and trapezo-metacarpal joint prostheses.

The technical field of the invention is the manufacture of phalangeal joint prostheses. These condylion type joints are characterized by their stability and their adaptability. The form of the joint serves as a guide and the ligamentary apparatus serves as a stabilizer for the joint and for the tendons. The joint prostheses of this invention are adaptable to the form of the object seized by the hand with a more less oblique/slanting flexion of the finger.

It thus appears that, in the study of the physiology of the mechanics of these joints, the couple articular surface/ligamentary apparatus is inseparable.

The goal of the invention is to achieve an articular prosthesis that reconstitutes the sliding surfaces and that preserves the ligamentary apparatus or permits its reconstruction.

2. Description of the Prior Art

Degenerative articular attacks on the metacarpo-phalangeal and inter-phalangeal joints are frequent; most often they are osteoarthritic in origin, but they can also occasionally be post-traumatic.

There are essentially two types of prosthesis: a first type of prosthesis, called a "spacer" is generally made of silicone and is in the form of a bellows. The disadvantages of spacers are a limited lifetime, lateral instability and a risk of silicone infection. A second type of prothesis, the "hinge" type, is contrary to the anatomy and provokes considerable constraints notably in rotation. Furthermore, this type of prosthesis can pose difficulties in the wear and tear on the hook/fastening representing the joint.

FR2 701 388 (Langanger-Landoes et al) discloses a prosthetic element for metacarpo- and inter-phalangeal joints that is comprised of three distinct pieces: a head with a convex or concave surface or a sliding joint, an inter-diaphyseal tail and a stem rigidly connecting the head and the tail on the inside. The surgeon can select a small number of each of the six distinct pieces, and make the desired prosthesis according to the anatomical-physiological characteristics of the patient.

The object of the present invention is to provide phalangeal joint prostheses. The solution to the problem posed consists of procuring a phalangeal joint prosthesis, for a metacarpo-phalangeal or inter-phalangeal joint, that consists of:

a head belonging to a proximal element, which includes a first articular sliding surface, a base belonging to distal element which includes a second articular sliding surface. Thes head and base are devoid of lateral or dorsal stops.

SUMMARY OF THE INVENTION

The invention permits a true movement related to the sliding of the head in relation to the base. Resection of the ligaments, particularly laterally; is avoided by use of this invention. By use of this invention one can avoid the osseous re-cut and removal of the implantation sites of these ligaments, thereby preserving the natural ligamentary apparatus or eventually permitting its reconstitution.

In a preferred embodiment of this invention:

the first and second sliding surfaces are more or less symmetrical in relation to a vertical anterior-posterior plane;

the first sliding surface is generally convex in form, not spherical, and is equipped in its palmar or lower central part with a portion of concave surface;

the second sliding surface is generally concave in form, not spherical, and is equipped in its palmar or lower central part with a portion of convex surface;

the curved radii (of the convex and concave parts) of the first sliding surface of the head are lower/smaller than the respective or corresponding curving radii (of the concave and convex parts) of the second sliding surface of the base;

the first and second sliding surfaces permit a relative movement of the head in relation to the base according to at least two degrees of freedom for an inter-phalangeal prosthesis and/or at least three degrees of freedom, preferably according to at least three rotations along three respective orthogonal axes, for a metacarpo-phalangeal prosthesis, as well as the relative displacement movements in translation of weak amplitude;

the proximal element of the prosthesis is composed of a head, an anchoring tail and an assembly element of the head and tail which permits at least the centering or alignment of the two pieces and prohibits a relative rotation movement between the two pieces (particularly a rotation movement along the longitudinal or diaphyseal axis);

the distal element is made up a base, an anchoring tail and an assembly element of the base and the anchoring tail;

the anchoring tail is metallic, generally cylindrical or like a flattened cone in shape, and is equipped with a hydroxyapatite coating on the external surface;

the base is comprised of a metallic sole and a body surmounting the sole and comprising the said second sliding surfaces. The sole is made of plastic material, such as polyethylene.

The invention provides improved prosthesis, which are perfectly anatomical, are modular, and will permit a true slide.

The shapes of the tail permit the assurance of an excellent primary fixation by a good filler (fill) of the medullary cavity, and an immediate (fit) blockage.

The coating permits the assurance of the secondary fixation by osseous colonization of the coating.

The active biomaterials (notably calcium phosphates including hydroxyapatite) have two essential qualities: they favor osseous regrowth and assure bone-implant continuity without intermediary formation of the fibrous tissue.

According to a mode of production, the layers of hydroxyapatite are set down by means of a plasma torch on an already structured metallic surface (of the tail) which permits the assurance of osteo-integration in the long run if the hydroxyapatite must subsequently be resorbed.

The form of the articular heads and bases of the prostheses according to the invention permit complete fulfillment of the function of these prostheses, essentially; to permit a flexion-extension movement, to assure a lateral stability with a little "play" to adapt the flexing finger to the object being sized by the hand, and to ensure the setting without force while permitting a "pumping". The modular character of the prostheses according to the invention permits, by the adaptation and the independent choice of the size of the tails, heads and bases, the adaptation to frequent morphological or anatomical variations, necessitating at times considerable articular surfaces while the medullar shafts are narrow or vice-versa (i.e., narrow surface, wide shaft).

In this case moreover, the osseous anchorage (without cement but covered by a hydroxyapatite coating or its equivalent) results in prolonging the life of the implant.

The numerous advantages provided by the invention will be better understood through the following description referring to the figures which illustrate without any limiting character the preferential modes of accomplishing the invention's phalangeal joint prostheses.

Except where otherwise indicated, the elements are marked by the same numbers from one figure to another.

BRIEF DESCRIPTION OF THE DRAWINGS

FIG. 1 schematically illustrates a cross section, by an interior-posterior vertical plane, the use of the metacarpo and interphalangeal prostheses according to the invention.

FIG. 2 is a view according to 11.11 of FIG. 1 and illustrates an inter-phalangeal prosthesis according to the invention in schematic cross section.

FIG. 3 is a schematic view in simplified perspective of a proximal element of the metacarpo-phalangeal prosthesis according to the invention.

FIG. 4 is a view in simplified perspective of a distal element of the metacarpo or inter-phalangeal prosthesis according to the invention capable of cooperating with the proximal element represented in FIG. 3.

DETAILED DESCRIPTION OF THE INVENTION

In reference to FIG. 1, the prostheses according to this invention permit the replacement of the joints between a metacarpal bone 13 and a first phalange 14 in order to constitute a prosthesis called metacarpo-phalangeal, and/or between two phalanges 14 and 15 in order to constitute an inter-phalangeal prosthesis.

An articular prosthesis is made up of a proximal element, such as found in 1 or 2, and of a distal element, such as found in 3 or 4.

The proximal element 1 is constituted of a head 5 extending to the extremity of the metacapal bone 13 and fixed in the medullary canal of the bone by a tail 16 in a more or less cylindrical or flattened cone form, to which the head 5 is fixed by an assembly element 20 such as, for example, a screw without a head lodged in a hole bored into the extremity of the fail 16 on one side and in the back part of the head 5 on the other.

The head 5 as represented in FIG. 1 is limited by two faces behind planes 26 and 27 creating an angle between them and by front face 9 generally convex in form and not spherical, which can be variable in shape in order to be adapted to the usually noted anatomy of the articular surfaces, that is to say endowed with multiple curved radii 25 defining the concave face 11 of the base 7 corresponding to the distal element 3 of the metacarpo-phalangeal joint.

This base 7 is preferably made up of a body 22 comprising the active joint face or surface 11 generally concave in form. The body 22 is, for example, made of plastic material such as polyethylene and is fixed on a sole 21, which is for example flat, preferably metallic, and is itself fixed to a tail 17 by an assembly element 20 such as previously explained.

The tail 17 is, like the tails found in 16, 18, 19 of the other parts of the prosthesis illustrated in FIG. 1, preferably lodged in the corresponding medullary canal without cement and preferably the external surface of the tails is covered in hydroxyapatite in order to favor osseous regrowth at the point of contact with the tail.

In a similar manner to that just described concerning the metacarpo-phalangeal prosthesis illustrated on the left side of FIG. 1, the inter-phalangeal prosthesis illustrated on the right side of this figure comprises a head 6 fixed to the extremity of a tail 18 by an assembly element 20 which can be either a screw or one (or several) pawns or spurs allowing the precise centering or alignment of the two pieces and inhibiting at least a rotation movement along the longitudinal axis of the tail between these two pieces (head and tail).

The head 6 is limited by a back surface 26 preferably flat and by a sliding from face 10, generally convex in form, possibly being made up a multitude of calottes/domes or portions of sphere radii 23,24 different (and equally different from the center) as represented on FIG. 1; the curved radii 23,24 have a lower/smaller value to the value of the curved radii 25 defining the concave surface 12, corresponding to the surface 10 and constituting the second sliding surface. In other words, the sliding surface of the base 8 corresponding to the head 6.

This base 8 is, as previously described for base 7, preferably made up of two parts: a body 22 fixed on a base 21 which is itself fixed to a tail 19 by assembly element 20.

By particular reference to FIG. 2, one sees that the first sliding face 10 (generally convex in form of the head 6 of the inter-phalangeal prosthesis) is in fact made up at least three parts: a first convex part 10a, a second central concave part 10b and a third convex part 10c, which is preferably more or less symmetrical to the first part 10a in comparison to an anterior-posterior vertical plane 30 passing by the longitudinal axis 29 of the tails 19 and 18 of the prosthesis's elements.

In a complementary manner, surface 12 (generally concave in form of the base 22 extending opposite head 6) is in fact made up of a first concave part 12 extending in correspondence to the part 10a of the head 6, a second central convex part 12b extending in correspondence with part 10b of the head 6, and a third concave part 12c extending opposite the convex part 10c of the head 6.

As illustrated in FIG. 3 the proximal element 1 of a metacarpo-phalangeal prosthesis includes said tail 16 to which is fixed the head 5 comprising a front face 9 generally convex in form which is in fact constituted by a first convex part 9a, of a second also convex part 9c and more or less symmetrical to part 9a in relation to the anterior-posterior plane 30 containing the axis 29 along which extends the tail 16.

In the lower or palmar and central part of the front face of the head 5 extends part 9b of the front face 9 which is concave and can extend opposite convex or protruding part 11b of the front face 11 of the corresponding base represented in FIG. 4, which as illustrated in this figure, is made up of a first concave part 11a, a second concave part 11c more or less symmetrical to the first part 11a in relation to said anterior-posterior plane 30 in general symmetry, which said first and second parts 11a and 11c are separated by a convex central (lower or palmar) part 11b.

Base 22, 7 of the distal element 3, represented in FIG. 4 is also fixed to a tail 17 fastening this part of the prosthesis to the phalange.

As FIG. 1 illustrates the prostheses according to the invention is characterized notably by a slight thickness 32 measured along the general longitudinal axis of the prosthesis, in relation to the biggest dimension or diameter 33; for example, the thickness 32 is less than half the largest dimension 33.

As FIG. 2 in particular illustrates the particular structure of the inter and metacarpophalangeal prostheses according to the invention permits their implantation to the extremities of the corresponding bones 14 and 15 without destroying the notably lateral zones of attachment of the ligaments 31 to bones 14 and 15 which permits the assurance of a satisfactory and anatomical functioning of the prosthesis.

As schematically represented in FIG. 3, the particular structure of the sliding faces or surfaces of the prostheses heads and bases according to the invention generally permits the relative displacement of the head in relation to the base according to, for example, three schematic rotations represented by the arrows 34, these rotations corresponding to the flexion/extension movements, of lateral slant and axial rotation, and can moreover permit a light movement relative to the translation between the head and the base equally along at least two orthogonal axes situated, for example, in a perpendicular plane to the longitudinal axis 29.

I claim:

1. A metacarpo-phalangeal joint prosthesis or an inter phalangeal joint prosthesis comprising:
   a proximal element comprising a head comprising a generally convex first sliding surface, and
   a first tail secured to said head for anchoring said proximal element in a medullary canal of a bone; and
   a distal element comprising: a base comprising a generally concave second sliding surface, a sole secured to said base, and a second tail secured to said sole for anchoring said distal element in a medullary canal of a bone, wherein curved radii of said head are smaller than corresponding curve radii of said base and wherein said base and said head are each devoid of stops to allow sliding of said first sliding surface with respect to said second sliding surface.

2. A modular metacarpo-phalangeal joint prosthesis or inter phalangeal joint prosthesis comprising: a proximal element comprising a head comprising a generally convex first sliding surface, and
   a first tail secured to said head for anchoring said proximal element in a medullary canal of a bone; and a distal element comprising a plastic base comprising a generally concave second sliding surface,
   a metallic sole element secured to said base, and
   a second tail secured to said sole for anchoring said distal element in a medullary canal of a bone; wherein said base and said head are each devoid of stops to flow sliding of said first sliding surface with respect to said second sliding surface, wherein curved radii of said head are smaller than corresponding curved radii of said base and a central part of said generally convex first sliding surface comprises a concave surface, and wherein a central part of said generally concave second sliding surface comprises a convex surface.

3. A metacarpo-phalangeal prosthesis according to claim 1 in which the first and second sliding surfaces permit a movement relative to the head in relation to the base of three schematic rotations and at least two orthogonal axes.

4. A metacarpo-phalangeal prosthesis according to claim 2 in which the first and second sliding surfaces permit a movement relative to the head in relation to the base of three schematic rotations and at least two orthogonal axes.

* * * * *